US006921731B2

United States Patent
Parlevliet et al.

(10) Patent No.: US 6,921,731 B2
(45) Date of Patent: Jul. 26, 2005

(54) PROCESS FOR REGENERATING PD CATALYSTS

(75) Inventors: Floris Jacobus Parlevliet, Amsterdam (NL); Johannes Gerardus Vries De, Maastricht (NL); Andreas Hendrikus Maria Vries De, Maastricht (NL)

(73) Assignee: DSM IP Assets B.V., Heerlen (NL)

( * ) Notice: Subject to any disclaimer, the term of this patent is extended or adjusted under 35 U.S.C. 154(b) by 108 days.

(21) Appl. No.: 10/297,237

(22) PCT Filed: Jun. 19, 2001

(86) PCT No.: PCT/NL01/00460

§ 371 (c)(1),
(2), (4) Date: Dec. 3, 2002

(87) PCT Pub. No.: WO02/00340

PCT Pub. Date: Jan. 3, 2002

(65) Prior Publication Data

US 2004/0029714 A1 Feb. 12, 2004

(30) Foreign Application Priority Data

Jun. 26, 2000 (NL) .............................................. 1015520

(51) Int. Cl.[7] ........................... B01J 20/34; B01J 23/44; B01J 38/42; B01J 38/54
(52) U.S. Cl. ........................... 502/32; 502/35; 502/325; 502/326
(58) Field of Search ........................... 502/32, 35, 325, 502/326; 558/274

(56) References Cited

U.S. PATENT DOCUMENTS 3,488,295 A * 1/1970 Glaser et al. ............... 502/26
3,700,729 A * 10/1972 Fenton ....................... 562/406
6,001,768 A * 12/1999 Buysch et al. .............. 502/230
6,005,151 A  12/1999 Herrmann et al. .......... 585/438
6,071,843 A  6/2000 Buysch et al. .............. 502/27

FOREIGN PATENT DOCUMENTS

WO  WO 98/49128  11/1998

OTHER PUBLICATIONS

Herrmann, W.A. et al., "Palladacycles as Structurally Defined Catalysts for the Heck Olefination of Chloro– and Bromoarenes" Angew. Chem. Ed. Engl. 34(17): 1844–1848 (1995).

* cited by examiner

*Primary Examiner*—Stanley S. Silverman
*Assistant Examiner*—Jonas N. Strickland
(74) *Attorney, Agent, or Firm*—Morrison & Foerster LLP

(57) ABSTRACT

Process for regenerating a Pd catalyst after a homogeneously catalyzed C—C coupling reaction in which the Pd catalyst precipitates, is separated from the reaction mixture and subsequently treated with $I_2$ or $Br_2$. The Pd catalyst can then be used in a subsequent reaction run.

Figure 1:
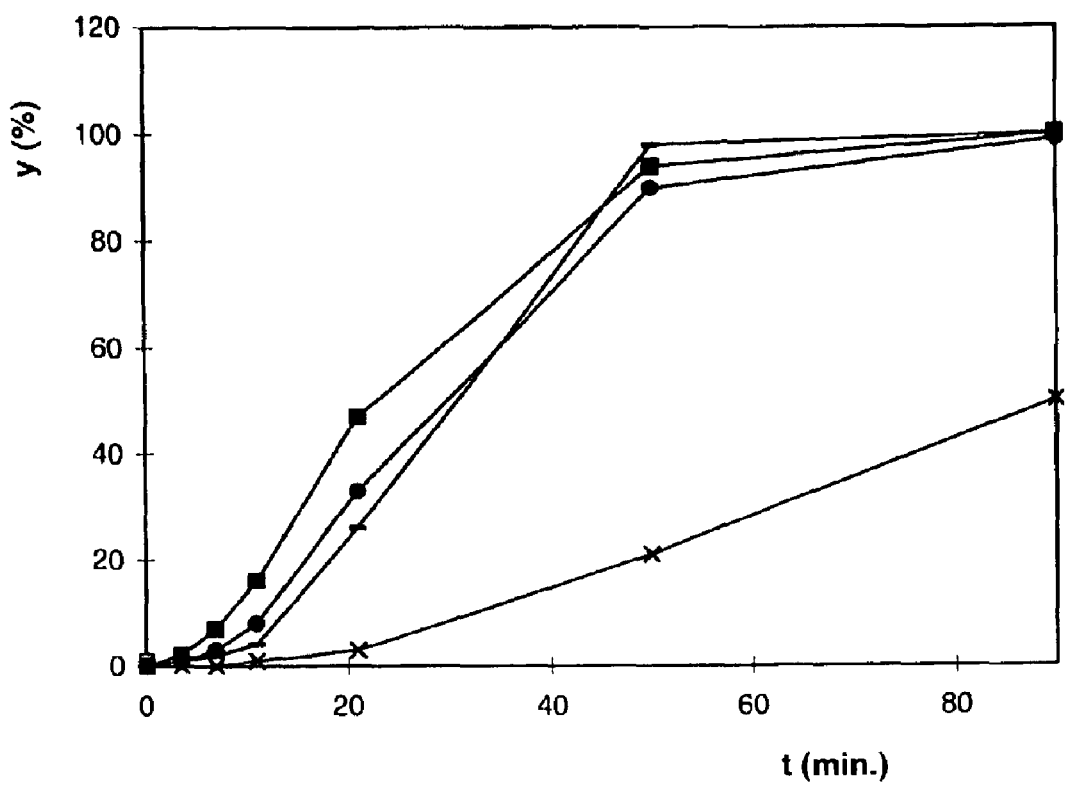

Preferably between 1 and 3 mole equivalents of $I_2$ or $Br_2$, relative to the quantity of Pd catalyst is used The C—C coupling reaction is preferably carried out in the presence of a support material.

The C—C coupling reaction may be for example a Heck reaction, a Suzuki reaction or a cross-coupling reaction.

15 Claims, 1 Drawing Sheet

PROCESS FOR REGENERATING PD CATALYSTS

CROSS-REFERENCE TO RELATED APPLICATION

This application is a national phase of PCT application PCT/NL01/00460 filed 19 Jun. 2001, which claims priority from European application 1015520 filed 26 Jun. 2000. The contents of these documents are incorporated herein by reference.

The invention relates to a process for regenerating Pd catalysts that precipitate and are separated from the reaction mixture after application in a homogeneously catalyzed C—C coupling reaction.

Homogeneously catalyzed C—C coupling reactions are known in the literature. Examples thereof are Heck reactions, Suzuki reactions and cross-coupling reactions. The costs of the catalyst used here are high, so that it is important to be able to reuse the catalyst. As a rule, strongly binding ligands are used in such reactions in order to keep the Pd catalyst in dissolved condition. A disadvantage of the application of such ligands, however, is that they are usually expensive and that the reaction mixture is more difficult to work up. When no strongly binding ligand or only a small amount of ligand relative to the Pd catalyst is used in the C—C coupling reaction, the Pd catalyst precipitates during or on completion of the reaction. It has been found, however, that when the precipitated catalyst, whether or not on a support, is recycled, the activity of the catalyst strongly declines.

Surprisingly it has now been found that when the Pd catalyst, after separation from the reaction mixture, is treated with $I_2$ or $Br_2$, the activity of the Pd catalyst is restored. The regenerated catalyst so obtained can then as such be used in a next run without further treatment or additives.

Preferably a support is added during the C—C coupling reaction in order to facilitate the catalyst being separated from the reaction mixture. Suitable support materials are for example the usual support materials for noble metal catalysts or filter aids, for example silica, alumina, diatomaceous earths, in particular celite and dicalite.

The weight ratio of support material to Pd is preferably 10 to 100, in particular 15–25.

The separation of the precipitated catalyst from the reaction mixture may, for example, be accomplished by filtration, decanting or centrifuging.

The quantity of $I_2$ or $Br_2$ to be used is preferably 0.1–10 mole equivalents, in particular 1–3 mole equivalents calculated relative to the quantity of Pd catalyst.

The temperature at which the treatment with $I_2$ or $Br_2$ takes place is not particularly critical and may for example be the room temperature. The treatment of the precipitated catalyst with $I_2$ or $Br_2$ is preferably performed in a solvent. The choice of solvent is not very critical as long as no undesired reaction takes place between solvent and the reagents. It may be advantageous to use the solvent that will be used in the subsequent C—C coupling reaction. Hereafter, the catalyst may be used for the next C—C coupling reaction. In a preferred embodiment of the process according to the invention the treatment with the iodine or bromine compound is carried out in situ during the subsequent reaction run, which means that the catalyst is separated from the reaction mixture after the reaction and is used as such in a subsequent reaction, with the $I_2$ or $Br_2$ being added, preferable as the first added reagent, in that subsequent reaction. Thus, in the latter case, the treatment with $I_2$ or $Br_2$ is carried out at the chosen reaction temperature.

Suitable solvents that may optionally be used in the C—C coupling reaction and in the treatment with $I_2$ or $Br_2$ are for example water, dipolar aprotic solvents, for example dimethylformamide (DMF), N-methylpyrrolidinone (NMP); aromatic hydrocarbons, in particular toluene; nitriles, in particular acetonitrile; esters, ethers, or ketones. Preferably a dipolar aprotic solvent or water is used as solvent.

In the context of the present invention, C—C coupling reactions are understood to be Pd-catalyzed aromatic and olefinic substitution reactions for instance those described in "Metal-catalyzed Cross-coupling Reactions" by F. Diederich and P. J. Stang Eds. Wiley-VCH, Weinheim 1998.

Examples of suitable C—C coupling reactions that can be carried out in the framework of the invention are Heck reactions, Suzuki reactions and cross-coupling reactions.

In the case of a Heck reaction, compounds of the RX type are substituted by an olefin, where X stands for a leaving group and R optionally stands for a substituted (hetero) aromatic group, a benzilic group or a vinylic group. The Heck reaction is carried out in the presence of a palladium compound, preferably in the presence of a base and preferably without a ligand.

Suitable examples of optionally substituted (hetero) aromatic groups are phenyl, naphthyl, pyridyl, pyrrolyl, quinolyl, isoquinolyl, furyl, thienyl, benzofuryl, indenyl, pyrimidinile, pyrazolyl, imidazolyl, p-methoxyphenyl, 6-methoxynaphtyl and p-isobutylphenyl. Benzilic groups are compounds with the formula Ar—C—, where C may or may not be substituted, provided that there is no H atom at the 1-position of the substituents, and Ar stands for an optionally substituted (hetero) aromatic group.

The (hetero) aromatic, benzilic and vinylic groups may be optionally substituted with 1 or more substituents, in principle any substituent that is inert under the given reaction conditions. Suitable examples of such substituents are an alkyl group, (hetero) aryl group, alkoxy group, cyano group, formyl group, alkylcarbonyl group, carboxyl group, carbamoyl group, nitro group or halogen.

The leaving group X of the RX compound is for example I, Br, OTf (triflate), $N_2^+Y^-$ in which Y stands for an anion, for example $Cl^-$ or $BF_4^-$, —C(O) Cl, —C(O) O C(O) Ar, $SO_2Cl$ of $SO_2^-Na^+$. Preferably I or Br is used as the leaving group.

As olefin use is preferably made of a compound with formula (1)

$$R^1R^2C=CHR^3 \qquad (1)$$

where $R^1$, $R^2$ and $R^3$ may each be chosen independently of each other in function of the desired final product and can stand for electropositive, electronegative and electroneutral groups. Suitable choices for $R^1$, $R^2$ and $R^3$ are hydrogen; an alkyl group with for example 1 to 20 carbon atoms; an alkenyl group with for example 2 to 20 carbon atoms; a (hetero) aryl group with for example 1 to 50 carbon atoms; a carboxyl group; an alkyl or arylcarboxylate group with for example 2 to 50 carbon atoms; an alkyl or arylacyl group with for example 2 to 50 carbon atoms; a carbamoyl group or an N-substituted alkyl or arylcarbamoyl group with for example 2 to 50 carbon atoms; an amino group or an N-substituted alkyl or arylamino group with for example 1 to 50 carbon atoms; an alkyl or arylamido group with for example 2 to 50 carbon atoms; an alkoxy group or aryloxy group with for example 1 to 50 carbon atoms; cyano; nitro;

a halogen or an alkyl or arylthio group with for example 1 to 50 carbon atoms.

Preferably one of the three substituents $R^1$, $R^2$, $R^3$ is hydrogen, more preferably two of the three substituents are hydrogen.

Suitable examples of olefins with formula (1) are aromatic and aliphatic alkenes, for example ethylene, 1,3-butadiene, 1-decene and styrene; acrylates, for example methylmethacrylate, n-butylacrylate, 2-ethyl-hexylacrylate, n-butylmethacrylate and benzylacrylate; olefinic nitriles, for example acrylonitrile and methacrylonitrile; olefinic amides, for example acrylamide and N,N-dimethylacrylamide; maleates, for example di-n-butylmaleate; pyridines, for example 4-vinylpyridine; olefinic ethers, for example cyclohexylvinyl ether and 1-vinyl-2-pyrrolidone. Also optionally substituted cyclic olefins, for example cyclohexene, indene and cyclooctene, where $R^1$ and $R^3$ from formula (1) form a ring structure together with the carbon atoms to which they are bound, are olefins that may suitably be used in the process according to the invention. Preferably aliphatic and aromatic alkenes and acrylates are used.

Suzuki reactions are known in literature, too; in Suzuki reactions an organoboron compound with the formula Ar—B($OR^4$)—$OR^5$, for example, where in practice Ar commonly represents a (hetero) aryl group and $R^4$ and $R^5$ each independently represent for example H or an alkyl group with for example 1–8 C atoms, or together with the O atoms to which they are bound and the B atom form a ring with 2–5 C atoms, is reacted with a compound with formula R—X as defined above for the Heck reaction.

Cross-coupling reactions are for example reactions in which an organometallic compound with formula $(R^6)_m$—M—$Q_n$, where $R^6$ stands for an alkyl group, vinyl group or aryl group with 1–18 C atoms, M stands for Li, Na, Mg, Zn, Al, Cu, Zr, Mn, Ni, B, Sn or Si, m=1, 2, 3 or 4 and n=0, 1, 2, or 3, Q may in principle be any group. Examples of $R^6_m$—M—$Q_n$ are $R^6$Li, $R^6$Na, $R^6$MgCl, $R^6$Al$(R^7)_2$, where the groups $R^7$ may each individually represent the same groups as $R^6$ except that when $R^6$ represents a vinyl group or an aryl group, $R^7$ is equal to alkyl, $R^6$ZnCl, $R^6$ZnBr, $R^6$B$(R^8)_2$, where the groups $R^8$ may each individually represent the same groups as $R^7$, $R^6$Sn$(C_4H_9)_3$, $R^6$ZrCp$_2$Cl (Cp=cyclopentadienyl), $R^6$Cu, $R^6$Cu(CN)Li, $R^6$Cu(CN)Znl, $R^6$Si$(CH_3)_3$, $R^6$SiF$_3$, $R^6$SiF$_2C_6H_5$, is contacted with a compound with formula R-X as defined above.

The C—C coupling reactions are preferably carried out in the presence of a base. The base is chosen preferably from the group of tertiary amines, aromatic heterocyclic bases, for example pyridine(s), alkalimetal acetates, alkalimetal hydroxides, alkalimetal phosphates, alkalimetal carbonates, and alkalimetal hydrogen carbonates. Suitable choices are NaOAc, KOAc, $K_2CO3$, $Na_2CO_3$, $Cs_2CO_3$ and $K_3PO_4$ or in a number of cases trialkylamines in which the alkyl groups each independently of each other preferably contain 1 to 20, in particular 1 to 5 carbon atoms, for example Me$_3$N, Et$_3$N, and n-Bu$_3$N.

The C—C coupling reaction is carried out in the process according to the invention with a Pd catalyst preferably without a ligand. Any Pd(0), Pd(II), and Pd(IV) compound may be used as a catalyst. As a Pd catalyst use is preferably made of Pd(OAc)$_2$, PdCl$_2$, PdBr$_2$, PdI$_2$, Na$_2$PdCl$_4$, Na$_2$PdCl$_6$, Pd$_2$(dba)$_3$ (dba=dibenzylidene acetone), PdCl$_2$(PhCN)$_2$, PdCl$_2$(CH$_3$CN)$_2$, Pd clusters, Pd metal, optionally on a support. The support material may be for example, alumina, carbon, or silica. In that case, extra addition of support material, as shown in the process of the invention, is not necessary.

The quantity of Pd catalyst to be used is not critical: preferably a quantity of 0.1–5 mole % is used, more preferably of 0.1–2 mole and most preferably 0.2–1 mole %, calculated relative to the quantity of RX.

The temperature at which the C—C coupling reaction is carried out is largely determined by the choice of the R—X compound and is preferably between 0 and 200° C., for example for R—I between 50 and 100° C. and for R—Br between 100 and 150° C.

The invention is further explained on the basis of the examples without being limited thereto.

EXAMPLES

Definitions
Yield=$C_{end}/D_0*100\%$ (Y)
Conversion=$(D_0-D_e)D_0*100\%$
Selectivity=(yield/conversion)*100% where:
$C_{end}$=number of moles of product that has been formed at the end of the reaction.
$D_0$=number of moles of RX at the beginning of the reaction.
$D_e$=number of moles of RX at the end of the reaction.

Example I

Regeneration of the Pd Catalyst with Iodine in the Heck Reaction of Phenyliodide and n-Butylacrylate In a 50 ml Schlenk vessel was weighed out: Pd(OAc)$_2$ (10.5 mg; 0.047 mmole, 0.24 mole % relative to phenyliodide) and 200 mg of Celite. 25 ml of NMP and a magnetic stirrer were added and the Schlenk vessel was sealed with a rubber septum. Under a nitrogen atmosphere there was subsequently added with the aid of a syringe while stirring: Et$_3$N (2.20 g, 21.8 mmole), dihexyl ether (2.0 mmole) as internal standard for GC analysis, and phenyliodide (4.1 g, 20.1 mmole). The reaction mixture was heated to 70° C., and n-butyl acrylate (3.25 g, 25.3 mmole) was added with the aid of a syringe. After a reaction time of 50 minutes at 70° C. the GC analysis indicated that the conversion was >95%, the yield was >90% and the selectivity was >95%.

The experiment was stopped after 90 minutes, and the reaction mixture was separated from the Pd that had precipitated on the celite with the aid of a centrifuge. The grey residue was returned to the Schlenk vesssel with 25 ml NMP and reactivated with I$_2$ (25 mg, 0.99 mmole, 2.1 mole equivalent relative to Pd(OAc)$_2$). The Schlenk vessel was again sealed with a rubber septum and the reagents required for the Heck reaction were added in a nitrogen atmosphere in the same way and in the same order as mentioned above.

After a reaction time of again 50 minutes at 70° C., GC analysis indicated that the conversion was >95%, the yield was >90% and the selectivity was >95%.

The experiment was stopped after 90 minutes and the reaction mixture was separated from the Pd that had precipitated on the Celite with the aid of a centrifuge.

With this technique the Heck reaction of phenyliodide and n-butyl acrylate could be carried out at least 7 times with practically the same conversions, yields and selectivities.

See FIG. 1 for the development of the Heck reaction (yield (Y) as a function of time (T)). For the sake of clarity only run 1 (_),2 (●) and 3(■) are shown along with the results of run 3 in a similar experiment without reactivation (X).

Example II

The same experiment, in which the grey residue with the precipitated Pd catalyst on Celite was each time washed with 25 ml of methyl-t-butyl ether (MTBE) before reactivating with iodine, produced the same results.

Example III

The same experiment, in which the grey residue with the precipitated Pd catalyst on Celite was each time reactivated with 2 mole equivalents bromine instead of iodine, produced the same results.

Example IV

The experiment cited in example III was repeated with silica being used instead of Celite. The same results were achieved.

Examples V–VII

Regeneration of the Pd catalyst with Iodine in the Pd (OAc)$_2$ catalyzed Heck Reaction of Different Arylhalogenides and Olefins The process according to example I was repeated using different arylhalogenides and/or olefins. The reaction conditions and the results of the first 2 runs are shown in table 1.

Example VIII

The process according to example I was repeated using K$_2$CO$_3$ (1.76 g, 12.8 mmole) and n-Bu$_4$NBr (1.70 g, 5.3 mmole) instead of Et$_3$N, and using water (29 ml) instead of NMP as solvent. After a reaction time of 120 minutes at 80° C. GC analysis indicated that the conversion was >95%, the yield was >90% and the selectivity was >95%.

The Pd that had precipitated on the Celite was separated, reactivated with iodine (32.7 mg, 0.13 mmole, 2.75 mole equivalents relative to Pd) and re-used in the Heck reaction of phenyliodide and n-butyl acrylate without loss of activity.

tivated with iodine (41.8 mg, 0.165 mmole, 1.9 mole equivalent relative to Pd(OAc)$_2$). The reagents required for the following run were added in a nitrogen atmosphere in the same way and in the same order as mentioned above. In the second run the same selectivity and activity were observed as in the first run.

What is claimed is:

1. A method for a homogeneously catalyzed C—C coupling, comprising conducting a C—C coupling using a Pd catalyst that is regenerated by treating a precipitated Pd catalyst, after separation from a reaction mixture, with iodine or bromine.

2. The method of claim 1, wherein the regenerated Pd catalyst is added to an additional reaction mixture for a C13 C coupling reaction.

3. The method of claim 2, wherein the ratio of equivalents of bromine or iodine to equivalents of precipitated and separated Pd catalyst is between 1 and 3.

4. The method of claim 2, wherein said Pd catalyst is Pd(OAc)$_2$, PdCl$_2$, PdBr$_2$, PdCl$_2$, Na$_2$PdCl$_4$, Na$_2$PdCl$_6$, Pd$_2$(dba)$_3$ (dba =dibenzyliden acetone), PdCl$_2$(PhCN)$_2$, PdCl$_2$(CH$_3$CN)$_2$, Pd clusters or Pd metal.

5. The method of claim 1, wherein said treating step is performed in situ in an additional reaction mixture for conducting a C—C coupling reaction.

6. The method of claim 5, wherein the ratio of equivalents of bromine or iodine to equivalents of precipitated and separated Pd catalyst is between 1 and 3.

7. The method of claim 5, wherein said Pd catalyst is Pd(OAc)$_2$, PdCl$_2$, PdBr$_2$, PdCl$_2$, Na$_2$PdCl$_4$, Na$_2$PdCl$_6$, Pd$_2$(dba)$_3$(dba=dibenzyliden acetone), PdCl$_2$(PhCN)$_2$, PdCl$_2$(CH$_3$CN)$_2$, Pd clusters or Pd metal.

8. The method of claim 1, wherein the ratio of equivalents of bromine or iodine to equivalents of precipitated and separated Pd catalyst is between 1 and 3.

TABLE 1

Examples V, VI and VII. (20 mmole aryl halogenide, 25 mmole olefin, 25 ml NMP, 13.5 mg Pd(OAc)$_2$ (0.3 mole %), 200–300 mg Celite).

| | | | | | Run 1 | | | | Run 2 | | | |
|---|---|---|---|---|---|---|---|---|---|---|---|---|
| Example | Aryl halide | ole-fin | Temp (° C.) | base | Time (hour) | conv. (%) | Yield (%) | selec. (%) | time (hour) | conv. (%) | yield (%) | selec. (%) |
| V | phenyliodide | styrene | 120 | Et$_3$N | 3 | 98 | 94 | 96 | 3 | 97 | 92 | 95 |
| VI | phenyliodide | cyclohexane | 140 | Et$_3$N | 2 | 98 | 92 | 94 | 2 | 90 | 81 | 90 |
| VII | 3bromopyr. | nbutylacryl. | 130 | NaOAc | 4 | 95 | 85 | 89 | 4 | 92 | 83 | 90 |

Example IX

Regeneration of the Pd Catalyst with Iodine in the Suzuki Coupling Reaction and the Cross-coupling Reaction In a 50 ml Schlenk vessel was weighed out: Pd(OAc)$_2$ (19 mg; 0.085 mmole, 0.5 mol % relative to 4-iodoanisole) and 300 mg Celite. 27 ml NMP and a magnetic stirrer were added. The reaction mixture was heated to 70° C. and the following was subsequently added in a nitrogen atmosphere while stirring: Et$_3$N (2.20 g, 21.8 mmole), dihexyl ether (2.0 mmole) as internal standard for GC analysis, 4-iodoanisole (4.15 g, 17.7 mmole) and phenylboronic acid (2.14 g, 17.5 mmole). The Schlenk vessel was sealed with a rubber septum and heated to 130° C. Sampling followed by GC analysis shows the formation of 2 products: the Suzuki product 4-phenylanisole and the cross-coupling product 4,4'-dimethoxybiphenyl. After a reaction time of 16 hours at 130° C. all 4-iodoanisole had been converted and the reaction was stopped.

The reaction mixture was separated from the Pd that had precipitated on the Celite using a centrifuge. The grey residue was washed with 25 ml diethyl ether, separated, and returned with 25 ml NMP to the Schlenk vessel and reac- 9. The method of claim 1, wherein said Pd catalyst is Pd(OAc)$_2$, PdCl$_2$, PdBr$_2$, PdCl$_2$, Na$_2$PdCl$_4$, Na$_2$PdCl$_6$, Pd$_2$(dba)$_3$(dba=dibenzylidene acetone), PdCl$_2$(PhCN)$_2$, PdCl$_2$(CH$_3$CN)$_2$, Pd clusters or Pd metal.

10. The method of claim 1, wherein the reaction mixture further contains a support material.

11. The method of claim 1, wherein the C—C coupling reaction is a Heck reaction.

12. The method of claim 1, wherein the C—C coupling reaction is a Suzuki reaction.

13. The method of claim 1, wherein the C—C coupling reaction is a cross-coupling reaction.

14. The method of claim 1, comprising conducting an additional C—C coupling using a precipitated Pd catalyst that is regenerated after separation from a first C—C coupling reaction mixture.

15. The method of claim 1, comprising conducting an additional C—C coupling using a precipitated Pd catalyst from a first C—C coupling reaction mixture, wherein iodine or bromine is added as a first reagent in said additional C—C coupling reaction.

* * * * *